United States Patent [19]

Nowatari et al.

[11] Patent Number: 4,737,589
[45] Date of Patent: Apr. 12, 1988

[54] PLATINUM COMPLEXES

[75] Inventors: Hiroyoshi Nowatari; Hiroshi Hayami, both of Takasaki; Yasuo Kuroda, Gunma; Sumio Yoda, Takasaki; Katsutoshi Takahashi, Tokyo, all of Japan

[73] Assignee: Nippon Kayaku Kabushiki Kaisha, Tokyo, Japan

[21] Appl. No.: 893,108

[22] Filed: Aug. 4, 1986

[30] Foreign Application Priority Data

Aug. 27, 1985 [JP] Japan .................. 60-187710
Feb. 12, 1986 [JP] Japan .................. 61-26799
Feb. 12, 1986 [JP] Japan .................. 61-26800
Apr. 25, 1986 [JP] Japan .................. 61-94626
Jul. 1, 1986 [JP] Japan .................. 61-152635

[51] Int. Cl.$^4$ .................................. C07F 15/00
[52] U.S. Cl. .................................. 556/137
[58] Field of Search .......................... 556/137

[56] References Cited

U.S. PATENT DOCUMENTS

| | | | |
|---|---|---|---|
| 4,250,189 | 2/1981 | Hydes et al. ........ | 556/137 X |
| 4,255,347 | 3/1981 | Kidani et al. . | |
| 4,410,544 | 10/1983 | Berg et al. ........ | 556/137 X |
| 4,431,666 | 2/1984 | Bulten et al. . | |
| 4,466,924 | 8/1984 | Verbeek et al. . | |
| 4,477,387 | 3/1984 | Kidani et al. . | |
| 4,482,569 | 11/1984 | Bulten et al. . | |
| 4,500,465 | 2/1985 | Amundsen et al. ........ | 556/137 X |
| 4,562,275 | 3/1984 | Speer et al. ........ | 556/137 |
| 4,598,091 | 7/1986 | Schonenberger et al. ..... | 556/137 X |
| 4,607,114 | 8/1986 | Nakayama et al. . | |

FOREIGN PATENT DOCUMENTS

| | | |
|---|---|---|
| 0055300 | 7/1982 | European Pat. Off. . |
| 16895 | 1/1982 | Japan . |
| 15641 | 6/1982 | Japan . |
| 156416 | 9/1982 | Japan . |

OTHER PUBLICATIONS

Chemical Abstracts, vol. 88, No. 20, Abstract No. 144630v.

Inorganica Chimica Acta, 26 (1978) L13–L14, Pahor et al.
Chemical Abstracts 93 125415r (1980).
Chemical Abstracts 95 423b (1981).

Primary Examiner—Helen M. S. Sneed
Attorney, Agent, or Firm—Banner, Birch, McKie and Beckett

[57] ABSTRACT

A diamine platinum (II) complex represented by the general formula

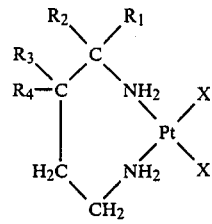

[wherein $R_1$, $R_2$, $R_3$ and $R_4$ are each a hydrogen atom or a lower alkyl group; and two X's are each a halogen atom or jointly form a group represented by

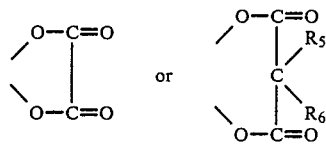

(wherein $R_5$ and $R_6$ are each a hydrogen atom or a lower alkyl group) or a group represented by

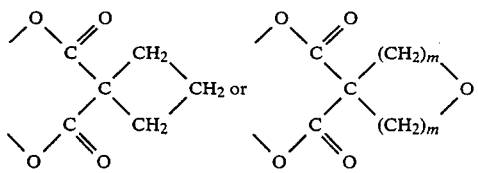

(wherein m is 1 or 2)].

5 Claims, No Drawings

PLATINUM COMPLEXES

BACKGROUND OF THE INVENTION

1. Field of the Invention

This invention relates to novel platinum complexes having an antitumor effect.

2. Description of the Prior Art

With respect to platinum complexes having an antitumor effect, cis-Platin (cis-dichlorodiammineplatinum) is already available commercially and is being applied to many cases because of its striking effect. Other platinum complexes having an antitumor effect as well are reported in several papers. Of these, platinum complexes having a straight alkyl diamine as a ligand are limited to those having a ligand represented by the general formula $$H_2N-C_nR_{2n}-NH_2 \quad (I)$$

(wherein R is a hydrogen atom or a substituent such as an alkyl group, a hydroxyl group or the like and n is an integer of 1 to 3). [e.g. Japanese Patent Application Kokai (Laid-Open) No. 156416/1982 or 103192/1981].

As mentioned above, cis-Platin is commercially available as a platinum complex carcinostatic agent. However, cis-Platin has high renal toxicity, which possess a dose limiting factor. Therefore, in administering cis-Platin, it is requisite that a large amount of water be administered before and during the administration of cis-Platin and that cis-Platin be administered together with a diuretics and over a long period of time. Further, cis-Platin, having low solubility in water and dissolving in water slowly, is supplied at a very low concentration. Furthermore, cis-Platin has very high vomitting toxicity, posing a problem in cure. Because of these drawbacks of cis-Platin, many researches have been conducted in order to find a platinum complex having an antitumor activity which has high solubility in water, low renal toxicity and low vomitting toxicity. However, no platinum complex has been applied practically till now.

SUMMARY OF THE INVENTION

When a 1,4-butanediamine or its derivative reacts with a platinum atom to form a coordination compound through the two nitrogen atoms of the diamine, there is formed a ring structure by 7 atoms including the platinum atom, namely, a 7-membered ring structure as shown in the formula (II) which appears later. In general, complexes having such a 7-membered ring structure are very difficult to synthesize in the usual way. As a result of an extensive research, the present inventors succeeded in the synthesis of various platinum (II) complexes having a 1,4-butanediamine or its derivative as a ligand and found that these complexes have an antitumor effect and that their renal toxicity and vomitting toxicity are remarkably lower than those of cis-Platin.

The present invention has been completed based on the above finding.

The present invention relates to diamine platinum (II) complexes represented by the general formula (II)

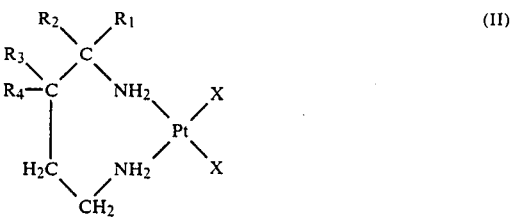

[wherein $R_1$, $R_2$, $R_3$ and $R_4$ are each a hydrogen atom or a lower alkyl group; and two X's are each a halogen atom or jointly form a group represented by

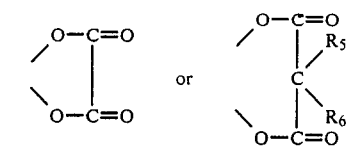

(wherein $R_5$ and $R_6$ are each a hydrogen atom or a lower alkyl group) or a group represented by

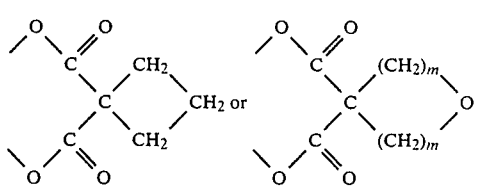

(wherein m is 1 or 2)].

DETAILED DESCRIPTION OF THE INVENTION

In the above general formula (II), the lower alkyls represented by $R_1$, $R_2$, $R_3$, $R_4$, $R_5$ and $R_6$ include, for example, alkyl groups of 1 to 4 carbon atoms. Specifically, there are mentioned a methyl group, an ethyl group, an n-propyl group, an isopropyl group, etc.

In the general formula (II), the halogen atom represented by X includes Cl, Br, etc.

Of the compounds of the present invention represented by the general formula (II), preferable are those where two X's jointly form a group represented by

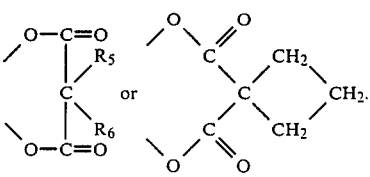

Also preferable are those where $R_1$ and $R_2$ represent each a hydrogen atom.

Typical examples of the compounds represented by the general formula (II) are shown below. However, the present invention is not restricted to these Examples.

1. cis-Dichloro-1,4-butanediamine platinum.
2. cis-Cyclobutane-1,1-dicarboxylato-1,4-butanediamine platinum.
3. cis-4-Oxacyclohexane-1,1-dicarboxylato-1,4-butanediamine platinum.
4. cis-Dichloro-1-methyl-1,4-butanediamine platinum.

5. cis-Oxalato-1-methyl-1,4-butanediamine platinum.
6. cis-Malonato-1-methyl-1,4-butanediamine platinum.
7. cis-Cyclobutane-1,1-dicarboxylato-1-methyl-1,4-butanediamine platinum.
8. cis-Dimethylmalonato-1-methyl-1,4-butanediamine platinum.
9. cis-Ethylmalonato-1-methyl-1,4-butanediamine platinum.
10. cis-Dichloro-1-ethyl-1,4-butanediamine platinum.
11. cis-Cyclobutane-1,1-dicarboxylato-1-ethyl-1,4-butanediamine platinum.
12. cis-4-Oxacyclohexane-1,1-dicarboxylato-1-ethyl-1,4-butanediamine platinum.
13. cis-Dichloro-2-methyl-1,4-butanediamine platinum.
14. cis-Malonato-2-methyl-1,4-butanediamine platinum.
15. cis-Cyclobutane-1,1-dicarboxylato-2-methyl-1,4-butanediamine platinum.
16. cis-4-Oxacyclohexane-1,1-dicarboxylato-2-methyl-1,4-butanediamine platinum.
17. cis-Dimethylmalonato-2-methyl-1,4-butanediamine platinum.
18. cis-Ethylmalonato-2-methyl-1,4-butanediamine platinum.
19. cis-Dichloro-2,2-dimethyl-1,4-butanediamine platinum.
20. cis-Oxalato-2,2-dimethyl-1,4-butanediamine platinum.
21. cis-Malonato-2,2-dimethyl-1,4-butanediamine platinum.
22. cis-Cyclobutane-1,1-dicarboxylato-2,2-dimethyl-1,4-butanediamine platinum.
23. cis-4-Oxacyclohexane-1,1-dicarboxylato-2,2-dimethyl-1,4-butanediamine platinum.
24. cis-Dimethylmalonato-2,2-dimethyl-1,4-butanediamine platinum.
25. cis-Dichloro-1,1-dimethyl-1,4-butanediamine platinum.
26. cis-Oxalato-1,1-dimethyl-1,4-butanediamine platinum.
27. cis-Cyclobutane-1,1-dicarboxylato-1,1-dimethyl-1,4-butanediamine platinum.
28. cis-Dimethylmalonato-1,1-dimethyl-1,4-butanediamine platinum.
29. cis-Dichloro-2-ethyl-1,4-butanediamine platinum.
30. cis-Oxalato-2-ethyl-1,4-butanediamine platinum.
31. cis-Malonato-2-ethyl-1,4-butanediamine platinum.
32. cis-Cyclobutane-1,1-dicarboxylato-2-ethyl-1,4-butanediamine platinum.
33. cis-Dimethylmalonato-2-ethyl-1,4-butanediamine platinum.
34. cis-Oxalato-2-isopropyl-1,4-butanediamine platinum.
35. cis-Dichloro-1,2-dimethyl-1,4-butanediamine platinum.

The compounds of the present invention can be produced by utilizing a known process, for example, a process described in Indian J. Chem. 8, 193 (1970) but it is necessary to modify the reaction method.

The compounds of the present invention can be produced by reacting a diamine represented by the general formula

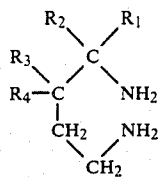

(wherein $R_1$, $R_2$, $R_3$ and $R_4$ have the same definitions as given previously, respectively) with

$M_2Pt(Hal)_4$ (wherein M is an atom capable of becoming a monovalent cation and Hal is a halogen atom) to obtain a dihalogenodiamine platinum complex represented by the general formula

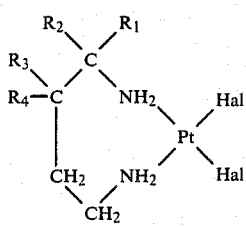

(wherein $R_1$, $R_2$, $R_3$ and $R_4$ and Hal have the same definitions as given previously, respectively) and, as necessary, reacting the dihalogenodiamine platinum complex with silver ions in the presence of water to convert to a diaquacomplex and reacting the diaquacomplex with a dicarboxylic acid or a salt thereof.

The production process of the compounds of the present invention will be described in more detail.

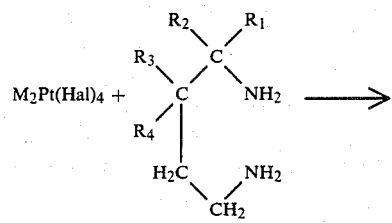

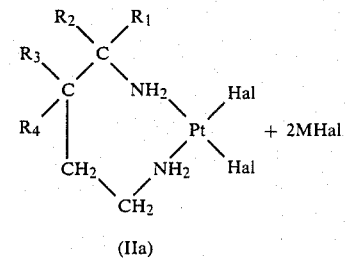

(IIa)

(In the above, M is an atom capable of becoming a monovalent cation, such as Na, K, Cs or the like; Hal is a halogen atom such as Cl, Br, I or the like; $R_1$, $R_2$, $R_3$ and $R_4$ have the same definitions as given previously, respectively.)

As shown in the above reaction scheme, a tetrahalogenoplatinate and a diamine are reacted in an aqueous medium, preferably water to obtain a dihalogenodiamine platinum. Water is used in an amount of preferably 5 to 500 liters, more preferably 5 to 160 liters, particularly preferably 20 to 80 liters per 1 mole of the tetrahalogenoplatinate. The diamine is used in an amount of preferably 0.5 to 4 moles, particularly preferably 0.9 to 1.2 moles per 1 mole of the tetrahalogenoplatinate. This reaction is conducted at 0° to 100° C., preferably 50° to 70° C. with stirring. In conducting the reaction, it is preferable that an aqueous tetrahalogenoplatinate solution and an aqueous diamine solution are gradually added to distilled water separately at the same time. The addition is conducted preferably slowly and usually takes 1 to 6 hours. The reaction can be conducted in an atmosphere of air but preferably under a stream of an inert gas such as nitrogen or the like.

Next, as shown in the following reaction scheme, the dihalogenodiamine platinum (IIa) is suspended in water and reacted with silver ions and the resulting silver halide precipitate is removed by filtration to obtain an aqueous solution of a diaquacomplex (III).

(IIa) + 2Ag⁺ + 2H₂O ———>

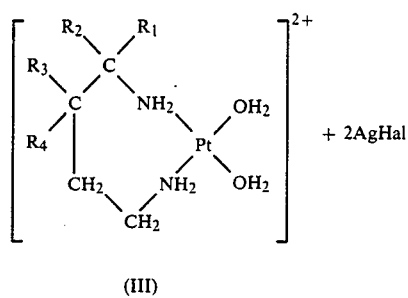

(III)

The water for suspending the dihalogenodiamine complex (IIa) can be used in an appropriate amount but the amount preferably is 5 to 150 l per 1 mole of the complex (IIa). The amount of silver ion has no particular restriction but, from an economical standpoint, is preferred to be 0.5 to 6 equivalents per 1 equivalent of the dihalogenodiamine complex (IIa). In order to avoid an excessive addition, the amount particularly preferably is 1.9 to 2 equivalents per 1 equivalent of the dihalogenodiamine complex (IIa). The reaction is conducted at 0° to 100° C., preferably 60° to 80° C. with stirring. As the compound generating silver ion, there can be used, for example, silver nitrate, silver sulfate, silver perchlorate and silver acetate.

Finally, the diaquacomplex (III) is reacted with a dicarboxylic acid salt, a dicarboxylic acid monohydrogen salt or a dicarboxylic acid. For example, the reaction is carried out by adding an aqueous solution containing an appropriate amount of a dicarboxylic acid salt, a dicarboxylic acid monohydrogen salt or a dicarboxylic acid to the aqueous solution of the diaquacomplex (III). Said salt or acid is used in an amount of preferably 0.5 to 10 moles, particularly preferably 0.9 to 6 moles per 1 mole of the diaquacomplex (III). The reaction can be conducted at 0° to 100° C. but preferably is conducted at 40° to 90° C. to obtain a compound (IIb).

(III) + Dicarboxylic acid salt or dicarboxylic acid monohydrogen salt or dicarboxylic acid ———>

-continued

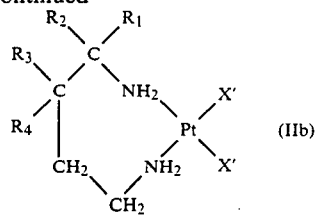

(In the above, X' is same as X other than halogen atoms.)

The structure of the compounds (II) of the present invention was confirmed by various analysis methods such as elemental analysis, infrared absorption spectrometry, fast atom bombardment mass spectrometry (FAB-MS $Pt^{194}$) and the like.

The compounds of the present invention have very low renal toxicity and very low vomitting toxicity, have high solubility in water, are dissolved in water rapidly, have an excellent antitumor effect, and accordingly are useful as an antitumor agent. When they are used as an antitumor agent, they can be administered as an injection, an oral drug and the like. Moreover, the compounds of the present invention are stable in air at room temperature, thus requiring no low temperature storage.

The embodiments of the present invention will be described below by way of Examples. However, the present invention is in no way restricted to these Example.

EXAMPLE 1 cis-Dichloro-1,4-butanediamine platinum (Compound No. 1)

10 g of potassium tetrachloroplatinate (II) was dissolved in 350 ml of water. Thereto was added a solution of 16 g of potassium iodide dissolved in 50 ml of water, with stirring. Stirring was continued for 5 minutes at 35° C. to obtain a black aqueous solution of potassium tetraiodoplatinate (II). Separately, 2.12 g of 1,4-butanediamine was dissolved in 400 ml of water to obtain an aqueous 1,4-butanediamine solution. 250 ml of water was placed in a flask. Into this water, were dropwise added the aqueous potassium tetraiodoplatinate (II) solution and the aqueous 1,4-butanediamine solution both prepared above, simultaneously for 2 hours at the constant rates, respectively while stirring at 60° C. The resulting reddish brown crystals were collected by filtration and washed with water, ethanol and ether in this order. The crystals were then dried under vacuum to obtain 9.74 g (yield: 75.3%) of crystals of cis-diiodo1,4-butanediamine platinum.

1 g of this product was suspended in 20 ml of water. Thereto was added a solution of 620 mg of silver nitrate dissolved in 10 ml of water. They were stirred for 20 minutes at 60° C. for reaction. The reaction mixture was cooled to room temperature and filtered to remove silver iodide. The silver iodide removed was washed with water. The filtrate and the washings were mixed together, and thereto was added a solution of 653 mg of sodium chloride dissolved in 5 ml of water. The mixture was stirred for 10 minutes at room temperature. The resulting yellow crystals were collected by filtration, washed with a small amount of water of 0° C. and then with ethanol, and dried under vacuum to obtain a compound No. 1.

Yield: 538 mg
Elementary analysis: Calculated (%): C 13.57, H 3.42, N 7.91, Pt 55.09; Found (%): C 13.44, H 3.56, N 8.04, Pt 54.8.
FAB-MS: $(M+H)^+ = 353$

EXAMPLE 2 cis-Cyclobutane-1,1-dicarboxylato-1,4-butanediamine Platinum (Compound No. 2)

In Example 1, the solution of 653 mg of sodium chloride dissolved in 5 ml of water was replaced by a solution obtained by dissolving 537 mg of 1,1-cyclobutanedicarboxylic acid in 7.26 ml of 1N aqueous sodium hydroxide solution. The mixture resulting from addition of this solution was stirred for 2 hours at 60° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 2.
Yield: 457 mg
Elementary analysis: Calculated (%): C 28.24, H 4.27, N 6.59, Pt 45.86; Found (%): C 28.56, H 4.41, N 6.48, Pt 45.2.
FAB-MS: $(M+H)^+ = 425$

EXAMPLE 3 cis-4-Oxacyclohexane-1,1-dicarboxylato-1,4-butanediamine platinum (Compound No. 3)

In Example 1, the solution of 653 mg of sodium chloride dissolved in 5 ml of water was replaced by a solution obtained by dissolving 324 mg of 4-oxacyclohexane-1,1-dicarboxylic acid in 7.26 ml of 1N aqueous sodium hydroxide solution. The mixture resulting from addition of this solution was stirred for 2 hours at 60° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 3.
Yield: 493 mg
Elementary analysis: Calculated (%): C 29.01, H 4.43, N 6.15, Pt 42.84; Found (%): C 28.76, H 4.62, N 6.04, Pt 42.4.
FAB-MS: $(M+H)^+ = 455$

EXAMPLE 4 cis-Dichloro-1-methyl-1,4-butanediamine platinum (Compound No. 4)

In Example 1, 2.46 g of 1-methyl-1,4-butanediamine was used in place of 2.12 g of 1,4-butanediamine and there were obtained 9.64 g (yield: 72.6%) of reddish brown crystals of cis-diiodo-1-methyl-1,4-butanediamine platinum. In the same manner as in Example 1 except that there were used 1 g of this product, 604 mg of silver nitrate and 636 mg of sodium chloride, a compound No. 4 was obtained as yellow crystals.
Yield: 400 mg
Elementary analysis: Calculated (%): C 16.31, H 3.83, N 7.61, Pt 52.99; Found (%): C 16.57, H 3.98, N 7.81, Pt 53.0.
FAB-MS: $(M+H)^+ = 367$

EXAMPLE 5 cis-Oxalato-1-methyl-1,4-butanediamine platinum (Compound No. 5)

In Example 4, 636 mg of sodium chloride was replaced by 669 mg of potasium oxalate monohydrate. After addition of a solution of 669 mg of this potassium oxalate monohydrate dissolved in 5 ml of water, the resulting mixture was stirred for 2 hours at 60° C. The resulting mixture was concentrated to 5 ml and then cooled to 0° C. The resulting white crystals were collected by filtration, washed with a small amount of water of 0° C. and then with ethanol, and dried under vacuum to obtain a compound No. 5.
Yield: 426 mg
Elementary analysis: Calculated (%): C 21.82, H 3.66, N 7.27, Pt 50.63; Found (%): C 22.01, H 3.71, N 6.98, Pt 52.0.
FAB-MS: $(M+H)^+ = 385$

EXAMPLE 6 cis-Malonato-1-methyl-1,4-butanediamine platinum (Compound No. 6)

In Example 4, the solution of 636 mg of sodium chloride dissolved in 5 ml of water was replaced by a solution obtained by dissolving 378 mg of malonic acid in 6.90 ml of 1N aqueous sodium hydroxide solution. The mixture resulting from addition of this solution was stirred for 8 hours at 50° C. The reaction mixture was concentrated to 5 ml and then cooled to 0° C. The resulting white crystals were collected by filtration, washed with a small amount of water of 0° C. and then with ethanol, and dried under vacuum to obtain a compound No. 6.
Yield: 305 mg
Elementary analysis: Calculated (%): C 24.06, H 4.04, N 7.02, Pt 48.85; Found (%): C 24.38, H 4.27, N 6.80, Pt 48.4.
FAB-MS: $(M+H)^+ = 399$

EXAMPLE 7 cis-Cyclobutane-1,1-dicarboxylato-1-methyl-1,4-butanediamine platinum (Compound No. 7)

In Example 4, the solution of 636 mg of sodium chloride dissolved in 5 ml of water was replaced by a solution obtained by dissolving 523 mg of cyclobutane-1,1-dicarboxylic acid in 7.08 ml of 1N aqueous sodium hydroxide solution. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 7.
Yield: 608 mg
Elementary analysis: Calculated (%): C 30.07, H 4.59, N 6.38, Pt 44.40; Found(%): C 29.88, H 4.44, N 6.53, Pt 44.1.
FAB-MS: $(M+H)^+ = 439$

EXAMPLE 8 cis-Dimethylmalonato-1-methyl-1,4-butanediamine platinum (Compound No. 8)

In Example 4, the solution of 636 mg of sodium chloride dissolved in 5 ml of water was replaced by a solution obtained by dissolving 480 mg of dimethylmalonic acid in 7.08 ml of 1N aqueous sodium hydroxide solution. The mixture resulting from addition of this solution was stirred for 6 hours at 50° C. The reaction mixture was concentrated to 5 ml and then cooled to 0° C. The resulting white crystals were collected by filtration, washed with a small amount of water of 0° C. and then with ethanol, and dried under vacuum to obtain a compound No. 8.

Yield: 532 mg

Elementary analysis: Calculated (%): C 28.11, H 4.72, N 6.55, Pt 45.65; Found (%): C 28.40, H 4.91, N 6.30, Pt 46.4.

FAB-MS: $(M+H)^+ = 427$

EXAMPLE 9 cis-Ethylmalonato-1-methyl-1,4-butanediamine platinum (Compound No. 9)

In Example 4, the solution of 636 mg of sodium chloride dissolved in 5 ml of water was replaced by a solution obtained by dissolving 480 mg of ethylmalonic acid in 7.08 ml of 1N aqueous sodium hydroxide solution. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 9.

Yield: 575 mg

Elementary analysis: Calculated (%): C 28.11, H 4.72, N 6.55, Pt 45.65; Found (%): C 27.88, H 4.65, N 6.48, Pt 46.1.

FAB-MS: $(M+H)^+ = 427$

EXAMPLE 10 cis-Dichloro-1-ethyl-1,4-butanediamine platinum (Compound No. 10)

In Example 1, 2.12 g of 1,4-butanediamine was replaced by 2.80 g of 1-ethyl-1,4-butanediamine and there were obtained 10.90 g (yield: 80.1%) of reddish brown crystals of cis-diiodo-1-ethyl-1,4-butanediamine platinum. In the same manner as in Example 1 except that 1 g of this product, 589 mg of silver nitrate and 620 mg of sodium chloride were used, a compound No. 10 was obtained as yellow crystals.

Yield: 394 mg

Elementary analysis: Calculated (%): C 18.86, H 4.22, N 7.33, Pt 51.04; Found (%): C 18.99, H 4.50, N 7.55, Pt 50.1.

FAB-MS: $(M+H)^+ = 381$

EXAMPLE 11 cis-Cyclobutane-1,1-dicarboxylate-1-ethyl-1,4-butanediamine platinum (Compound No. 11)

In Example 10, the solution of 620 mg of sodium chloride dissolved in 5 ml of water was replaced by a solution obtained by dissolving 510 mg of cyclobutanedicarboxylic acid in 6.90 ml of 1N aqueous sodium hydroxide solution. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 11.

Yield: 342 mg

Elementary analysis: Calculated (%): C 31.79, H 4.89, N 6.18, Pt 43.03; Found (%): C 31.53, H 4.71, N 6.36, Pt 42.6.

FAB-MS: $(M+H)^+ = 453$

EXAMPLE 12 cis-4-Oxacyclohexane-1,1-dicarboxylato-1-ethyl-1,4-butanediamine platinum (Compound No. 12)

In Example 10, the solution of 620 mg of sodium chloride dissolved in 5 ml of water was replaced by a solution obtained by dissolving 616 mg of 4-oxacyclohexane-1,1-dicarboxylic acid in 7.08 ml of 1N aqueous sodium hydroxide solution. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 12.

Yield: 321 mg

Elementary analysis: Calculated (%): C 32.30, H 5.00, N 5.79, Pt 40.35; Found (%): C 32.51, H 5.12, N 6.01, Pt 39.2.

FAB-MS: $(M+H)^+ = 483$

EXAMPLE 13 cis-Dichloro-2-methyl-1,4-butanediamine platinum (Compound No. 13)

In Example 1, 2.12 g of 1,4-butanediamine was replaced by 2.46 g of 2-methyl-1,4-butanediamine and there were obtained 9.94 g (yield: 74.9%) of reddish brown crystals of cis-diiodo-2-methyl-1,4-butanediamine platinum. In the same manner as in Example 1 except that 1 g of this product, 604 mg of silver nitrate and 636 mg of sodium chloride were used, a compound No. 13 was obtained as yellow crystals.

Yield: 238 mg

Elementary analysis: Calculated (%): C 16.31, H 3.83, N 7.61, Pt 52.99; Found (%): C 16.15, H 3.70, N 7.44, Pt 53.1.

FAB-MS: $(M+H)^+ = 367$

EXAMPLE 14 cis-Malonato-2-methyl-1,4-butanediamine platinum (Compound No. 14)

In Example 13, the solution of 636 mg of sodium chloride dissolved in 5 ml of water was replaced by a solution obtained by dissolving 227 mg of malonic acid in 4.36 ml of 1N aqueous sodium hydroxide solution. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 14.

Yield: 125 mg

Elementary analysis: Calculated (%): C 24.06, H 4.04, N 7.02, Pt 48.85; Found (%): C 24.22, H 3.99, N 7.41, Pt 49.4.

FAB-MS: $(M+H)^+ = 399$

EXAMPLE 15 cis-Cyclobutane-1,1-dicarboxylato-2-methyl-1,4-butanediamine platinum (Compound No. 15)

A compound No. 15 was obtained as white crystals in the same manner as in Example 14 except that the solution obtained by dissolving 227 mg of malonic acid in 4.36 ml of 1N aqueous sodium hydroxide solution was replaced by a solution obtained by dissolving 523 mg of cyclobutane-1,1-dicarboxylic acid in 7.29 ml of 1N aqueous sodium hydroxide solution.

Yield: 131 mg
Elementary analysis: Calculated (%): C 30.07, H 4.59, N 6.38, Pt 44.40; Found (%): C 30.20, H 4.31, N 6.15, Pt 44.5.
FAB-MS: $(M+H)^+ = 439$

EXAMPLE 16 cis-4-Oxacyclohexane-1,1-dicarboxylato-2-methyl-1,4-butanediamine platinum (Compound No. 16)

A compound No. 16 was obtained in the same manner as in Example 15 except that 523 mg of cyclobutane-1,1-dicarboxylic acid was replaced by 632 mg of 4-oxacyclohexane-1,1-dicarboxylic acid.

Yield: 171 mg
Elementary analysis: Calculated (%): C 30.71, H 4.72, N 5.97, Pt 41.56; Found (%): C 30.28, H 4.88, N 6.10, Pt 42.0.
FAB-MS: $(M+H)^+ = 469$

EXAMPLE 17 cis-Dimethylmalonato-2-methyl-1,4-butanediamine platinum (Compound No. 17)

A compound No. 17 was obtained in the same manner as in Example 15 except that 523 mg of cyclobutane-1,1-dicarboxylic acid was replaced by 480 mg of dimethylmalonic acid.

Yield: 141 mg
Elementary analysis: Calculated (%): C 28.11, H 4.72, N 6.56, Pt 45.65; Found (%): C 27.80, H 4.52, N 6.26, Pt 45.4.
FAB-MS: $(M+H)^+ = 427$

EXAMPLE 18 cis-Ethylmalonato-2-methyl-1,4-butanediamine platinum (Compound No. 18)

A compound No. 18 was obtained in the same manner as in Example 15 except that 523 mg of cyclobutane-1,1-dicarboxylic acid was replaced by 480 mg of ethylmalonic acid.

Yield: 124 mg
Elementary analysis: Calculated (%): C 28.11, H 4.72, N 6.56, Pt 45.65; Found (%): C 27.60, H 4.91, N 6.10, Pt 45.2.
FAB-MS: $(M+H)^+ = 427$

EXAMPLE 19 cis-Dichloro-2,2-dimethyl-1,4-butanediamine platinum (Compound No. 19)

In Example 1, 2.12 g of 1,4-butanediamine was replaced by 2.80 g of 2,2-dimethyl-1,4-butanediamine and there were obtained 11.20 g (yield: 82.3%) of yellowish brown crystals of cis-diiodo-2,2-dimethyl-1,4-butanediamine platinum. In the same manner as in Example 1 except that 1 g of this product, 589 mg of silver nitrate and 620 mg of sodium chloride were used, a compound No. 19 was obtained as yellow crystals.

Yield: 283 mg
Elementary analysis: Calculated (%): C 18.86, H 4.22, N 7.33, Pt 51.04; Found (%): C 19.12, H 4.03, N 7.01, Pt 50.8.
FAB-MS: $(M+H)^+ = 381$

EXAMPLE 20 cis-Oxalato-2,2-dimethyl-1,4-butanediamine platinum (Compound No. 20)

In Example 19, the solution of 620 mg of sodium chloride dissolved in 5 ml of water was replaced by a solution of 652 mg of potassium oxalate monohydrate dissolved in 5 ml of water. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 20.

Yield: 448 mg
Elementary analysis: Calculated (%): C 24.06, H 4.04, N 7.02, Pt 48.85; Found (%): C 23.99, H 4.11, N 6.86, Pt 49.3.
FAB-MS: $(M+H)^+ = 399$

EXAMPLE 21 cis-Malonato-2,2-dimethyl-1,4-butanediamine platinum (Compound No. 21)

A compound No. 21 was obtained as white crystals in the same manner as in Example 20 except that the solution of 652 mg of potassium oxalate monohydrate dissolved in 5 ml of water was replaced by a solution obtained by dissolving 368 mg of malonic acid in 6.90 ml of 1N aqueous sodium hydroxide solution.

Yield: 331 mg
Elementary analysis: Calculated (%): C 26.15, H 4.39, N 6.78, Pt 47.20; Found (%): C 26.51, H 4.55, N 6.41, Pt 46.1.
FAB-MS: $(M+H)^+ = 413$

EXAMPLE 22 cis-Cyclobutane-1,1-dicarboxylato-2,2-dimethyl-1,4-butanediamine platinum (Compound No. 22)

A compound No. 22 was obtained as white crystals in the same manner as in Example 20 except that the solution of 652 mg of potassium oxalate monohydrate dissolved in 5 ml of water was replaced by a solution obtained by dissolving 510 mg of cyclobutane-1,1-dicarboxylic acid in 6.90 ml of 1N aqueous sodium hydroxide solution.

Yield: 375 mg
Elementary analysis: Calculated (%): C 31.79, H 4.89, N 6.18, Pt 43.03; Found (%): C31.81, H 5.01, N 6.36, Pt. 43.2
FAB-MS: $(M+H)^+ = 453$

EXAMPLE 23 cis-4-Oxacyclohexane-1,1-dicarboxylato-2,2-dimethyl-1,4-butanediamine platinum (Compound No. 23)

A compound No. 23 was obtained as white crystals in the same manner as in Example 20 except that the solution of 652 mg of potassium oxalate monohydrate dissolved in 5 ml of water was replaced by a solution obtained by dissolving 616 mg of 4-oxacyclohexane-1,1- dicarboxylic acid in 6.90 ml of 1N aqueous sodium hydroxide solution.

Yield: 326 mg

Elementary analysis: Calculated (%): C 32.30, H 5.00, N 5.79, Pt 40.35; Found (%): C 33.11, H 4.97, N 6.01, Pt 39.8

FAB-MS: $(M+H)^+ = 483$

EXAMPLE 24 cis-Dimethylmalonato-2,2-dimethyl-1,4-butanediamine platinum (Compound No. 24)

A compound No. 24 was obtained as white crystals in the same manner as in Example 20 except that the solution of 652 mg of potassium oxalate monohydrate dissolved in 5 ml of water was replaced by a solution obtained by dissolving 467 mg of dimethylmalonic acid in 6.90 ml of 1N aqueous sodium hydroxide solution.

Yield: 407 mg

Elementary analysis: Calculated (%): C 29.93, H 5.02, N 6.35, Pt 44.20; Found (%): C 30.14, H 5.28, N 6.19, Pt 43.9.

FAB-MS: $(M+H)^+ = 441$.

EXAMPLE 25 cis-Dichloro-1,1-dimethyl-1,4-butanediamine platinum (Compound No. 25)

In Example 1, 2.12 g of 1,4-butanediamine was replaced by 2.80 g of 1,1-dimethyl-1,4-butanediamine and there were obtained 10.62 g (yield: 78.0%) of reddish brown crystals of cis-diiodo-1,1-dimethyl-1,4-butanediamine platinum. In the same manner as in Example 1 except that 1 g of this product, 589 mg of silver nitrate and 620 mg of sodium chloride were used, a compound No. 25 was obtained as yellow crystals.

Yield: 264 mg

Elementary analysis: Calculated (%): C 18.86, H 4.22, N 7.33, Pt 51.04; Found (%): C 18.77, H 4.33, N 7.58, Pt 50.7.

FAB-MS: $(M+H)^+ = 381$

EXAMPLE 26 cis-Oxalato-1,1-dimethyl-1,4-butanediamine platinum (Compound No. 26)

In Example 25, the solution of 620 mg of sodium chloride dissolved in 5 ml of water was replaced by a solution of 652 mg of potassium oxalate monohydrate dissolved in 5 ml of water. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 26.

Yield: 433 mg

Elementary analysis: Calculated (%): C 24.06; H 4.04, N 7.02, Pt 48.85; Found: (%): C 24.31, H 4.22, N 7.01, Pt 49.2.

FAB-MS: $(M+H)^+ = 399$

EXAMPLE 27 cis-Cyclobutane-1,1-dicarboxylato-1,1-dimethyl-1,4-butanediamine platinum (Compound No. 27)

A compound No. 27 was obtained as white crystals in the same manner as in Example 26 except that the solution of 652 mg of potassium oxalate monohydrate dissolved in 5 ml of water was replaced by a solution obtained by dissolving 510 mg of cyclobutane-1,1-dicarboxylic acid in 6.9 ml of 1N aqueous sodium hydroxide solution.

Yield: 207 mg

Elementary analysis: Calculated (%): C 31.79, H 4.89, N 6.18, Pt 43.03; Found (%): C 32.02, H 5.11, N 6.01, Pt 44.2.

FAB-MS: $(M+H)^+ = 453$

EXAMPLE 28 cis-Dimethylmalonato-1,1-dimethyl-1,4-butanediamine platinum (Compound No. 28)

A compound No. 28 was obtained as white crystals in the same manner as in Example 27 except that 510 mg of cyclobutane-1,1-dicarboxylic acid was replaced by 467 mg of dimethylmalonic acid.

Yield: 337 mg

Elementary analysis: Calculated (%): C 29.93, H 5.02, N 6.35, Pt 44.20; Found (%): C 30.22, H 5.36, N 6.10, Pt 43.4.

FAB-MS: $(M+H)^+ = 441$

EXAMPLE 29 cis-Dichloro-2-ethyl-1,4-butanediamine platinum (Compound No. 29)

In Example 1, 2.12 g of 1,4-butanediamine was replaced by 2.80 g of 2-ethyl-1,4-butanediamine and there were obtained 10.32 g (yield: 75.8%) of reddish brown crystals of cis-diiodo-2-ethyl-1,4-butanediamine platinum. In the same manner as in Example 1 except that 1 g of this product, 589 mg of silver nitrate and 620 mg of sodium chloride were used, a compound No. 29 was obtained as yellow crystals.

Yield: 257 mg

Elementary analysis: Calculated (%): C 18.86, H 4.22, N 7.33, Pt 51.04; Found (%): C 19.00, H 4.35, N 7.16, Pt 51.0.

FAB-MS: $(M+H)^+ = 381$

EXAMPLE 30 cis-Oxalato-2-ethyl-1,4-butanediamine platinum (Compound No. 30)

In Example 29, the solution of 620 mg of sodium chloride dissolved in 5 ml of water was replaced by a solution of 652 mg of potassium oxalate monohydrate dissolved in 5 ml of water. The mixture resulting from addition of this solution was stirred for 2 hours at 60° C. The reaction mixture was concentrated to 5 ml and then cooled to 0° C. The resulting white crystals were collected by filtration, washed with a small amount of water of 0° C. and then with ethanol, and dried under vacuum to obtain a compound No. 30.

Yield: 428 mg

Elementary analysis: Calculated (%): C 24.06, H 4.04, N 7.02, Pt 48.85; Found (%): C 24.33, H 4.17, N 6.96, Pt 48.5.

FAB-MS: $(M+H)^+ = 399$

EXAMPLE 31 cis-Malonato-2-ethyl-1,4-butanediamine platinum (Compound No. 31)

A compound No. 31 was obtained in the same manner as in Example 30 except that the solution of 652 mg of potassium oxalate monohydrate dissolved in 5 ml of water was replaced by a solution obtained by dissolving 368 mg of molonic acid in 6.90 ml of 1N aqueous sodium hydroxide solution.

Yield: 280 mg

Elementary analysis: Calculated (%): C 26.15, H 4.39, N 6.78, Pt 47.20; Found (%): C 26.53, H 4.50, N 6.59, Pt 46.1.

FAB-MS: $(M+H)^+ = 413$

EXAMPLE 32 cis-Cyclobutane-1,1-dicarboxylato-2-ethyl-1,4-butanediamine platinum (Compound No. 32)

A compound No. 32 was obtained in the same manner as in Example 31 except that 368 mg of malonic acid was replaced by 510 mg of cyclobutane-1,1-dicarboxylic acis.

Yield: 451 mg

Elementary analysis: Calculated (%): C 31.79, H 4.89, N 6.18, Pt 43.03; Found (%): C 31.51, H 4.67, N 6.22, Pt 42.1.

FAB-MS: $(M+H)^+ = 453$

EXAMPLE 33 cis-Dimethylmalonato-2-ethyl-1,4-butanediamine platinum (Compound No. 33)

A compound No. 33 was obtained in the same manner as in Example 31 except that 368 mg of malonic acid was replaced by 467 mg of dimethylmalonic acid.

Yield: 361 mg

Elementary analysis: Calculated (%): C 29.93, H 5.02, N 6.35, Pt 44.20; Found (%): C 30.14, H 5.18, N 6.19, Pt 45.2.

FAB-MS: $(M+H)^+ = 441$

The physical characteristics of the compounds of the present invention are shown in Table 1.

TABLE 1

| Compound No. | Solubility in water (mg/ml) | IR absorption spectrum (cm$^{-1}$) N—H | C=O |
|---|---|---|---|
| 1 | >2* | 3250–3150 | — |
| 2 | >5 | 3210–3130 | 1650–1610 |
| 3 | >10 | 3230–3120 | 1670–1630 |
| 4 | >2* | 3240–3150 | — |
| 5 | >3 | 3220–3140 | 1700–1685 |
| 6 | >10 | 3260–3090 | 1640–1600 |
| 7 | >5 | 3220–3110 | 1660–1600 |
| 8 | >20 | 3230–3140 | 1640–1590 |
| 9 | >10 | 3250–3110 | 1630–1590 |
| 10 | >2* | 3230–3120 | — |
| 11 | >3 | 3210–3100 | 1650–1600 |
| 12 | >5 | 3230–3090 | 1680–1620 |
| 13 | >2* | 3248–3225 | — |
| 14 | >50 | 3200–3125 | 1730–1610 |
| 15 | >8 | 3200–3125 | 1700–1620 |
| 16 | >15 | 3200–3130 | 1690–1610 |
| 17 | >20 | 3250–3125 | 1680–1640 |
| 18 | >10 | 3190–3120 | 1710–1620 |
| 19 | >2* | 3220–3130 | — |
| 20 | >3 | 3260–3140 | 1690–1660 |
| 21 | >5 | 3190–3120 | 1680–1610 |
| 22 | >3 | 3220–3130 | 1620–1600 |
| 23 | >3 | 3230–3130 | 1650–1590 |
| 24 | >10 | 3250–3140 | 1640–1590 |
| 25 | >2* | 3210–3130 | — |
| 26 | >3 | 3220–3140 | 1700–1660 |
| 27 | >10 | 3220–3130 | 1640–1600 |
| 28 | >10 | 3240–3140 | 1640–1590 |
| 29 | >2* | 3220–3130 | — |
| 30 | >3 | 3240–3120 | 1690–1660 |
| 31 | >10 | 3230–3130 | 1680–1600 |
| 32 | >5 | 3220–3130 | 1630–1590 |

TABLE 1-continued

| Compound No. | Solubility in water (mg/ml) | IR absorption spectrum (cm$^{-1}$) N—H | C=O |
|---|---|---|---|
| 33 | >10 | 3240–3150 | 1650–1600 |

*Solubility in physiological saline solution

In view of the fact that cis-Platin has solubility of about 1.2 mg/ml in physiological saline solution, the present compounds apparently have high solubility in water. In addition, the present compounds are dissolved in water quickly. Therefore, when used as an injection, the crystals of the present compounds can be dissolved in water prior to administration and the resulting aqueous solutions can be administered immediately after dissolution.

Next, the antitumor activities of the present compounds will be described by way of Experimental Examples.

EXPERIMENTAL EXAMPLE 1

Growth inhibition test on cultured mouse leukemia L1210 cells (Test method)

Mouse leukemia L1210 cells were cultured in a RPMI 1640 medium containing 10% of fetal calf serum. Inhibition percentage (%) of growth was calculated from the numbers of cells in the cases of addition and no addition of each compound, and IC$_{50}$ value (a concentration at which growth was inhibited by 50%) was obtained from a graph prepared by plotting a concentration of compound and the inhibition percentage on a logarithmic probability paper.

The results are shown in Table 2.

TABLE 2

| Compound No. | IC$_{50}$ (μg/ml) |
|---|---|
| 1 | 0.33 |
| 2 | 0.88 |
| 3 | 0.65 |
| 4 | 0.20 |
| 5 | 0.29 |
| 6 | 0.76 |
| 7 | 2.80 |
| 8 | 0.90 |
| 9 | 2.40 |
| 10 | 0.35 |
| 11 | 4.70 |
| 12 | 1.05 |
| 13 | 0.10 |
| 14 | 0.74 |
| 15 | 1.20 |
| 16 | 0.43 |
| 17 | 0.50 |
| 18 | 0.84 |
| 19 | 0.20 |
| 20 | 0.37 |
| 21 | 0.72 |
| 22 | 2.20 |
| 23 | 0.44 |
| 24 | 0.78 |
| 25 | 0.25 |
| 26 | 0.30 |
| 28 | 4.50 |
| 29 | 0.05 |
| 30 | 0.06 |
| 31 | 0.66 |
| 32 | 0.67 |
| 33 | 0.23 |

As is obvious from Table 2, the compounds of the present invention show an inhibition activity on the growth of cancer cells at a low concentration.

The present compounds show an excellent inhibition activity also on the growth of cis-Platin resistant tumor cells which have acquired a resistance to cis-Platin as a result of its administration. An experimental example on this activity will be described on the compound No. 15 as an example.

EXPERIMENTAL EXAMPLE 2

Growth inhibition test on cis-Platin resistant tumor cells (Test method)

$1 \times 10^5$ mouse leukemia L1210 cells or $1 \times 10^5$ mouse leukemia P388 cells were inoculated into the abdominal cavities of $CDF_1$ female mouse. After 2 days from the inoculation, 6 mg/kg of cis-Platin was administered to them intraperitoneally. After 5 days, their tumor cells were inoculated to the abdominal cavities of other $CDF_1$ female mouse, and the same treatment was applied. By repeating this procedure, cis-Platin resistant tumor cells were obtained.

Using the tumor cells thus obtained, test for growth inhibition activity was conducted in the same manner as in Experimental Example 1, whereby $IC_{50}$ for cis-Platin resistant tumor cells (hereinafter referred to as $IC_{50}R$) was obtained. Then, the ratio of this $IC_{50}R$ to $IC_{50}$ for tumor cells having no cis-Platin resistance, namely, $IC_{50}R/IC_{50}$ was calculated.

The results are shown in Table 3.

TABLE 3

| Compound No. | $IC_{50}R/IC_{50}$ Tumor cell L1210 | Tumor cell P388 |
| --- | --- | --- |
| Cis-Platin | 11.4 | 10.7 |
| 15 | 3.19 | 3.26 |

As is obvious from Table 3, the present compounds show an inhibition activity also on the growth of cis-Platin resistant tumor cells, at a low concentration.

EXPERIMENTAL EXAMPLE 3

Antitumor activity test on mouse leukemia L1210 in vivo (Test method)

$1 \times 10^5$ mouse leukemia L1210 cells were inoculated into the abdominal cavities of 6-week-old female $CDF_1$ mice. From the next day, a compound was administered to them intraperitoneally once a day for 5 consecutive days. Mice of compound-non-treated group (control group) were administered with physiological saline solution in the same manner. The average survival times of the compound-treated group and the control group (abbreviated as T and C, respectively) were measured and T/C percentage (T/C × 100) was calculated from the following equation.

$$T/C = \frac{\text{Average survival time of compound-treated group}}{\text{Average survival time of control group}} \times 100$$

When any mouse died during the test due to the acute toxicity of the compound administered, 50% lethal dose ($LD_{50}$) was calculated according to the conventional method.

The results are shown in Table 4. In Table 4, max (T/C) means the maximum value of T/C and optimum dose (opt. dose) means an administration amount giving the max (T/C), namely, an optimum administration amount.

TABLE 4

| Compound No. | max (T/C) | Opt. dose (mg/kg) | $LD_{50}$ (mg/kg) |
| --- | --- | --- | --- |
| 1 | 203 | 2 | 4.8 |
| 2 | 182 | 32 | 48.0 |
| 3 | 132 | 8 | 8.4 |
| 4 | 225 | 2 | 2.4 |
| 5 | 273 | 4 | 6.0 |
| 6 | 359 | 32 | 48.0 |
| 7 | 176 | 64 | — |
| 8 | 189 | 64 | — |
| 9 | 222 | 64 | 96.0 |
| 10 | 210 | 4 | 6.0 |
| 11 | 139 | 64 | — |
| 12 | 181 | 64 | — |
| 13 | 187 | 2 | 4.2 |
| 14 | 346 | 32 | — |
| 15 | 182 | 32 | 80.0 |
| 16 | 167 | 8 | 12.0 |
| 17 | 238 | 32 | — |
| 18 | 264 | 16 | 24.0 |
| 19 | 359 | 4 | 6.0 |
| 20 | 272 | 8 | 12.0 |
| 21 | 301 | 32 | 48.0 |
| 22 | 320 | 128 | — |
| 23 | 159 | 32 | — |
| 24 | 253 | 64 | — |
| 25 | 150 | 2 | 3.0 |
| 29 | 261 | 2 | 3.0 |
| 30 | 253 | 8 | — |
| 32 | 275 | 32 | — |

As is obvious from Table 4, the compounds of the present invention have a life prolongation effect for mice inoculated with mouse leukemia L1210 cells.

The compounds of the present invention have life prolongation effects also for mice inoculated with tumor cells other than mouse leukemia L1210 cells. These effects will be explained in Experimental Example 4 on the compound No. 15 as an example.

EXPERIMENTAL EXAMPLE 4

Antitumor activity test on various tumors in vivo (Test method)

$1 \times 10^6$ mouse leukemia P388 cells were inoculated into the abdominal cavities of 6-week-old female $CDF_1$ mice, and from the next day a compound No. 15 was administered to them intraperitoneally once a day for 5 consecutive days. Separately, $1 \times 10^6$ mouse lung cancer Lewis lung carcinoma (LL) cells were inoculated into the abdominal cavities of male $BDF_1$ mice, and from the next day a compound No. 15 was administered to them intraperitoneally once a day for 5 consecutive days. Separately, $1 \times 10^6$ mouse fibrosarcoma M5076 cells were inoculated into the body sides of female C57BL/6 mice subcutaneously, and from the next day a compound No. 15 was administered to them intraperitoneally. Separately, $1 \times 10^6$ mouse colon cancer (colon 26) cells were inoculated into the abdominal cavities of female $CDF_1$ mice, and from the next day a compound No. 15 was administered to them intraperitoneally. To respective control groups (compound-non-treated groups), physiological saline solution was administered.

From the survival times of the compound-treated group and the control group, respective median values (median survival times) were calculated. Using these values, T/C percentage was calculated from the following equation.

$$T/C = \frac{\text{Median survival time of compound-treated group}}{\text{Median survival time of control group}} \times 100$$

The results are shown in Table 5.

TABLE 5

| Tumor cell | Antitumor activity of compound No. 15 on various tumor cells | |
|---|---|---|
| | Max (T/C) | Opt. dose (mg/kg) |
| P388 | 260 | 32 |
| LL | 222 | 32 |
| M5076 | 152 | 16 |
| Colon 26 | 198 | 32 |

As is obvious from Table 5, the compounds of the present invention have a striking life prolongation effect for mice inoculated with various tumor cells.

Next, the renal toxicity of the present compounds will be described by way of an Experimental Example.

EXPERIMENTAL EXAMPLE 5

Test for renal toxicity (Test method)

A compound was administered one time to 6-week-old male CDF$_1$ mice intraperitoneally. After 4 days, their blood was collected for measurement of blood urea nitrogen concentration (BUN value).

The results are shown in Table 6. The optimum dose of cis-Platin was 4 mg/kg according to the test method of Example 3, but in the above renal toxicity test, a BUN value far higher than the normal value (30 mg/dl or lower) is seen even when cis-Platin was administered in an amount of four times the optimum dose. Based on this fact, as shown in Table 6, the administration amount of the present compound employed in this Experimental Example was 4 times the optimum dose obtained in Experimental Example 3, or more. In Table 6, body weight ratio is a ratio of body weight after 4 days from administration to body weight of administration day.

TABLE 6

| Compound No. | Administration amount (mg/kg) | Body weight ratio | BUN value (mg/dl) |
|---|---|---|---|
| Physiological salt solution | — | 1.05 | 22.7 |
| cis-Platin | 16 | 0.72 | 92.9 |
| 1 | 8 | 0.83 | 11.4 |
| 2 | 128 | 0.73 | 16.2 |
| 4 | 8 | 0.75 | 28.4 |
| 5 | 16 | 0.76 | 12.9 |
| 6 | 128 | 0.75 | 24.6 |
| 7 | 256 | 0.85 | 13.1 |
| 8 | 256 | 0.71 | 25.4 |
| 10 | 16 | 0.74 | 21.3 |
| 11 | 256 | 1.09 | 23.2 |
| 12 | 256 | 0.94 | 16.8 |
| 13 | 20 | 0.74 | 22.6 |
| 14 | 128 | 0.72 | 15.9 |
| 15 | 240 | 0.74 | 19.8 |
| 17 | 128 | 0.73 | 16.7 |
| 18 | 64 | 0.74 | 19.6 |
| 19 | 16 | 0.76 | 15.7 |
| 20 | 32 | 0.75 | 13.5 |
| 21 | 128 | 0.76 | 16.7 |
| 22 | 512 | 0.74 | 14.4 |
| 23 | 128 | 0.89 | 15.0 |
| 24 | 256 | 0.79 | 19.7 |
| 25 | 8 | 0.79 | 16.8 |
| 29 | 8 | 0.72 | 18.1 |
| 30 | 32 | 0.87 | 18.2 |
| 32 | 128 | 0.74 | 19.7 |

As is obvious from Table 6, the BUN value obtained when the present compound is administered is very lower than the value obtained when commercially available cis-Platin is administered, and is close to the value obtained whey physiological saline solution is administered. This indicates that the present compounds have very low renal toxicity. Accordingly, the present compounds can be used as an antitumor agent of very low renal toxicity. In view of this characteristics and high solubility in water, the present compounds, when intraveneously injected, can be applied not in continuous administration but in bolus administration.

Some of the present compounds have, as a ligand, a diamine having an asymmetric carbon atom. Such an amine was subjected to optical resolution to obtain its optical isomers. Using these isomers as a ligand, respective complexes were synthesized and tested. These syntheses and tests will be described on the compound No. 15 as examples, by way of Examples and Experimental Examples.

EXAMPLE 34

R-2-methyl-1,4-butanediamine 40 g of R-3-methyladipic acid was added to a mixture of 200 g of concentrated sulfuric acid and 320 ml of benzene. The mixture was heated at 45° C. using a water bath to dissolve 3-methyladipic acid. To this solution was added 56 g of sodium azide gradually, and the mixture was subjected to reaction at 45° to 50° C. After the completion of the addition, stirring was continued for 10 minutes. Then, a saturated solution containing 200 g of sodium hydroxide was added dropwise. The resulting sodium sulfate precipitate was removed by filtration and the benzene phase in the filtrate was separated. The water phase of the filtrate was extracted with 500 ml of benzene, with 500 ml of ether and lastly with 500 ml of chloroform four times. All the extracts were mixed together and dehydrated with anhydrous sodium sulfate. Sodium sulfate was removed by filtration and the filtrate was concentrated using a rotary evaporator. The concentrate was subjected to vacuum distillation to obtain R-2-methyl-1,4-butanediamine.

Yield: 6.92 g (yield: 27.1%)
Boiling point: 83° C./30 mmHg
Purity: 99.3%
Optical purity: 100%

In this Example and the following Example, purity and optical purity were determined according to methods such as gas chromatography, optical rotation measurement and the like.

EXAMPLE 35

Isolation of optical isomers of 2-methyl-1,4-butanediamine by optical resolution 2-methyl-1,4-butanediamine was subjected to optical resolution by converting it into a salt with dibenzoyltartaric acid and recrystallizing the salt (the two optical isomers have different solubilities). For obtaining R-2-methyl-1,4-butanediamine, (−)-dibenzoyltartaric acid was used, and for obtaining S-2-methyl-1,4-butanediamine, (+)-dibenzoyltartaric acid was used. The resolution yields, purities and optical purities of the two isomers of 2-methyl-1,4-butanediamine are shown in Table 7.

TABLE 7

|  | Resolution yield (%) | Purity (%) | Optical purity (%) |
| --- | --- | --- | --- |
| R-isomer | 57.8 | 100 | 98.6 |
| S-isomer | 51.4 | 100 | 98.8 |

Using the optical isomers obtained in Examples 34 and 35 and in the same manner as in Example 15, there were obtained cis-cyclobutane-1,1-dicarboxylato-R-2-methyl-1,4-butanediamine platinum (compound No. 15R) and cis-cyclobutane-1,1-dicarboxylato-S-2-methyl-1,4-butanediamine platinum (compound No. 15S). Table 8 shows the synthesis yields and elementary analysis of these complexes when synthesized from potassium tetrachloroplatinate (II), and Table 9 shows their physical properties. the $(M+H)^+$ values of the complexes when measured by means of FAB-MS were both 439.

TABLE 8

| Compound No. | Synthesis yield (%) | Elementary analysis (%) | | | |
| --- | --- | --- | --- | --- | --- |
| | | C | H | N | Pt |
| 15R | 24.6 | 29.98 | 4.43 | 6.22 | 44.8 |
| 15S | 23.1 | 30.21 | 4.37 | 6.36 | 45.0 |

TABLE 9

| Compound No. | Solubility in water (mg/ml) | IR absorption spectrum $(cm^{-1})$ | |
| --- | --- | --- | --- |
| | | N—H | C=O |
| 15R | >15 | 3200–3125 | 1700–1620 |
| 15S | >15 | 3210–3130 | 1700–1620 |

The optical isomers 15R and 15S were subjected to the same tests as in Experimental Example 1 and Experimental Example 3. The results are shown in Table 10.

TABLE 10

| Compound No. | IC$_{50}$ (μg/ml) | max (T/C) | Opt. dose (mg/kg) | LD$_{50}$ (mg/kg) |
| --- | --- | --- | --- | --- |
| 15R | 0.78 | 189 | 32 | 33.6 |
| 15S | 1.08 | 206 | 32 | 48.0 |

The optical isomers 15R and 15S were also subjected to the same test as in Experimental Example 4. The results are shown in Table 11.

TABLE 11

| Compound No | Tumor cell | max (T/C) | Opt. dose (mg/kg) |
| --- | --- | --- | --- |
| 15R | P388 | 253 | 20 |
| 15R | LL | 166 | 30 |
| 15S | P388 | 253 | 40 |
| 15S | LL | 164 | 50 |

The optical isomers 15R and 15S were subjected to the same renal toxicity test as in Experimental Example 5. The results are shown in Table 12. The administration dose of each compound was four times the optimum dose shown in Table 10.

TABLE 12

| Compound No. | Administration amount (mg/kg) | Body weight ratio | BUN value (mg/dl) |
| --- | --- | --- | --- |
| 15R | 128 | 0.71 | 10.6 |
| 15S | 128 | 0.90 | 21.4 |

As is obvious from the above experimental results, both 15R and 15S have high solubility in water, show excellent antitumor activities on various tumor cells and have very low renal toxicity.

EXAMPLE 36

(Compound No. 5)

In Example 4, the solution of 636 mg of sodium chloride dissolved in 5 ml of water was replaced by a solution of 343 mg of oxalic acid dihydrate dissolved in 5 ml of water. The mixture resulting from addition of this solution was stirred for 24 hours at 40° C. The reaction mixture was concentrated to 5 ml and then cooled to 0° C. The resulting white crystals were collected by filtration, washed with a small amount of water of 0° C. and then with ethanol, and dried under vacuum to obtain a compound No. 5. The compound had the same analysis values as the compound No. 5 of Example 5.

EXAMPLE 37

(Compound No. 4)

In Example 4, the solution of 604 mg of silver nitrate dissolved in 10 ml of water was replaced by a solution of 560 mg of silver sulfate dissolved in 150 ml of water. The mixture resulting from addition of this solution was stirred for 20 minutes at 80° C. The subsequent procedure was same as in Example 4, whereby a compound No. 4 was obtained as yellow crystals. The compound had the same analysis value as the compound No. 4 of Example 4.

The compounds of the present invention show an growth inhibition activity on the tumor cells at low concentrations and accordingly have a very excellent antitumor effect against various kinds of tumor. The present compounds have high solubility in water and are quickly dissolved in water. The present compounds have low renal toxicity and low vomitting toxicity. Further, the present compounds are mild with respect to bone marrow toxicity which is generally seen with the conventional platinum complex antitumor agents; that is, the decrease in the number of white blood cells occurs mainly and their toxicity to platelets is very slight. Furthermore, recovery to normal conditions is very rapid and accordingly control is easy when the present compounds are used as an antitumor agent. Based on these facts, the present compounds can be used as an excellent antitumor agent. Moreover, the present compounds are stable in air at room temperature, thus requiring no low temperature storage.

What is claimed is:

1. cis-Cyclobutane-1,1-dicarboxylato-2-methyl-1,4-butanediamine platinum.
2. cis-Cyclobutane-1,1-dicarboxylato-2-ethyl-1,4-butanediamine platinum.
3. cis-Cyclobutane-1,1-dicarboxylato-R-2-methyl-1,4-butanediamine platimum.
4. cis-Cyclobutane-1,1-dicarboxylato-S-2-methyl-1,4-butanediamine platinum.
5. A diamine platinum (II) complex represented by the general formula

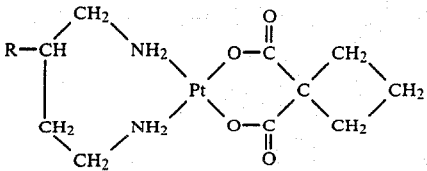

wherein R is a lower alkyl group.